(12) United States Patent
Lin et al.

(10) Patent No.: US 8,399,029 B2
(45) Date of Patent: Mar. 19, 2013

(54) INFLUENZA PREVENTION AND TREATMENT COMPOSITION

(75) Inventors: Jian-Er Lin, Hong Kong (CN); Kee Hung Chu, Hong Kong (CN)

(73) Assignee: Ultra Biotech Limited, Douglas Isle of Man (GB)

( * ) Notice: Subject to any disclaimer, the term of this patent is extended or adjusted under 35 U.S.C. 154(b) by 0 days.

(21) Appl. No.: 13/335,972

(22) Filed: Dec. 23, 2011

(65) Prior Publication Data

US 2012/0156190 A1 Jun. 21, 2012

Related U.S. Application Data

(63) Continuation-in-part of application No. 12/015,177, filed on Jan. 16, 2008, now abandoned.

(60) Provisional application No. 60/885,729, filed on Jan. 19, 2007.

(51) Int. Cl.
*A01N 65/00* (2009.01)
(52) U.S. Cl. ........................................................ 424/725
(58) Field of Classification Search ........................ None
See application file for complete search history.

(56) References Cited

U.S. PATENT DOCUMENTS 6,068,846 A * 5/2000 Cho et al. ...................... 424/730

* cited by examiner

*Primary Examiner* — Michael Meller
(74) *Attorney, Agent, or Firm* — Duane Morris LLP; Siegfried J. W. Ruppert

(57) ABSTRACT

A composition for influenza prevention and treatment includes bio-transformed soy and St. John's wort.

7 Claims, 4 Drawing Sheets

Protection against H9N1 Challenge in Mice

Fig. 1

INFLUENZA PREVENTION AND TREATMENT COMPOSITION

CROSS-REFERENCE TO RELATED APPLICATION

This application is a continuation-in-part (CIP) of prior U.S. application Ser. No. 12/015,177, filed on Jan. 16, 2008 now abandoned, which claims priority to U.S. Provisional Application No. 60/885,729, filed on Jan. 19, 2007. The contents of both prior applications are incorporated herewith by reference.

FIELD OF THE INVENTION

The present application related to disease treatment or prevention. Particularly, it relates to a method of treating and preventing influenza using a composition containing an immune enhancer and an anti-viral agent.

BACKGROUND OF THE INVENTION

Influenza, or commonly known as flu, is a contagious respiratory illness caused by influenza viruses. Influenza spreads around the world in seasonal epidemics, killing millions of people in pandemic years and hundreds of thousands in non-pandemic years. Typically, influenza is transmitted from infected mammals through the air and from infected birds through their droppings. Moreover, influenza infects many animal species, and transfer of viral strains between species can occur. Birds are thought to be the main animal reservoirs of influenza viruses.

Ways to prevent or inactivate influenza viruses in humans may include vaccination and anti-viral medications. An influenza vaccine is recommended for high-risk groups, such as children and the elderly, but the effectiveness of those influenza vaccines is variable. Due to the high mutation rate of the virus, a particular influenza vaccine usually confers protection for no more than a few years. Moreover, it is possible to get vaccinated and still get influenza. Anti-viral medication is sometimes effective, but viruses can develop resistance to even the standard anti-viral drugs, such as amantadine, rimantadine, zanamavir and oseltamivir.

Consequently, developing flu preventing and treating products with high efficacy are desirable. New and effective compositions are needed to prevent and treat the influenza viruses including avian flu viruses.

SUMMARY OF THE INVENTION

According to one aspect, a composition for influenza treatment includes an immune enhancer and an anti-viral agent.

According to another aspect, a method of treating influenza includes administrating to a mammal the influenza prevention and treatment composition.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF THE DRAWINGS

FIG. 1 depicts the efficacy of the composition to protect against H9N1 virus challenge in mice.

DETAILED DESCRIPTION OF PARTICULAR EMBODIMENTS OF THE INVENTION

Figure 2:
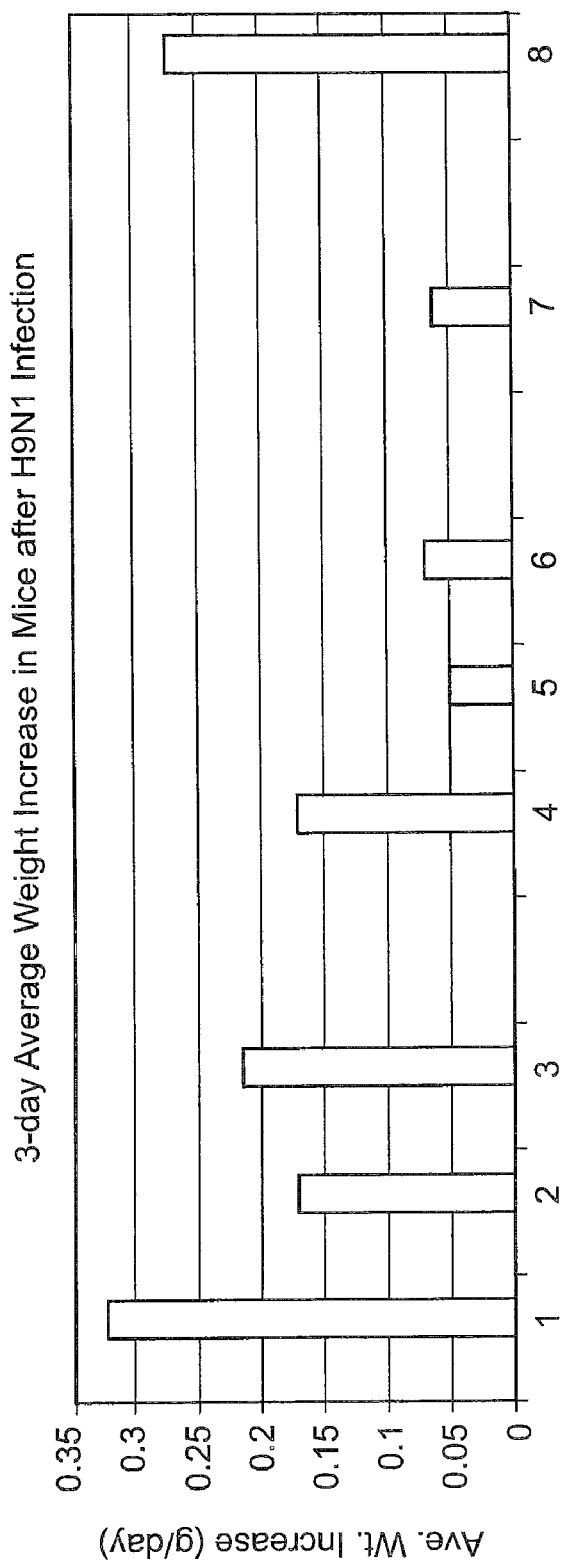
FIG. 2 depicts the efficacy of the composition of FIG. 1 compared to the composition without either an immune enhancer or an anti-viral agent.

Reference will now be made in detail to a particular embodiment of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims. In addition, improvements and modifications which may become apparent to persons of ordinary skill in the art after reading this disclosure, the drawings, and the appended claims are deemed within the spirit and scope of the present invention.

A composition for influenza prevention and treatment includes an immune enhancer and an anti-viral agent. The immune enhancer may include one or more agents that increase the immunity of a mammal under in-vitro, in-vivo animal or human testing. In one example, the immune enhancer is a bio-transformed soy, which is produced by Ultra Biotech Limited (a wholly owned subsidiary of CK Life Sciences Int'l. (Holdings), Inc.) in Hong Kong, China. The process of making the bio-transformed soy is disclosed below in detail. In another example, the immune enhancer is an immune enhancing protein, such as lactoferrin and immunoglobulins, lingzhi, cordyceps, and tinospora ingredients. The concentration of the immune enhancer in the composition may range from 1 to 99 weight percent (wt %), but preferably from 5 to 95 wt %.

The anti-viral agent of the composition is configured to inactivate the function or reduce the effectiveness of an invading flu virus, and thus may include any agent that has that effect on the flu viruses. For example, the anti-viral agent may be St. John's wort, which is an extract or any part of the *Hypericum perforatum* plant, or a purified compound of the *Hypericum perforatum* plant, or a man-made synthesized compound of the *Hypericum perforatum* plant, such as hypericin and pseudohypericin. Other examples of the anti-viral agents may include adamantane, oseltamivir, zanamivir, amantadine and rimantadine.

The concentration of the anti-virus agent in the composition may range from 1 to 99 wt %, but preferably from 10 to 90 wt %. In one example, the anti-viral agent includes St. John's wort from about 20 mg to 5,000 mg. In another example, the anti-viral agent includes St. John's wort from about 100 mg to 2,000 mg. The anti-viral agent may also include 0.3% w/w of hypericin.

The specific concentrations of the immune enhancer and anti-virus agent may vary depending on the use. In one example, the composition may include 12.5 wt % of the immune enhancer and 87.5 wt % of the anti-virus agent. In another example, the composition may include 45 wt % of the immune enhancer and 55 wt % of the anti-virus agent. Other inert ingredients, such as filler and flavoring agent, may also be incorporated into the composition.

The function of the composition may include protecting a subject from being infected, minimizing the effect of an invading flu virus and accelerating the recovery from a virus infection when and if a subject is infected. In particular, the composition may be used to prevent the infection of the flu and to treat flu symptoms after a viral infection, including avian flu viruses of H9N1 and H5N1.

The composition may be in a tablet, capsule or liquid form, and may be adapted for oral administration, injections and other methods.

EXAMPLE 1

In-Vitro Tests—Anti-Flu Virus (H9N1)

Flu virus, H9N1, was added into each of the 96-well plate at the initial concentration of 0.5, 5, 50 and 500 plague formation units per well (or pfu/well), respectively. The composition for influenza prevention and treatment was then dissolved in 2% serum-containing DMEM medium, and added into the wells at 8, 40 and 200 ppm, respectively. The medium without the composition was used as a control. The plates were incubated at 37° C. and at 5% $CO_2$ for three days. The H9N1 virus counts were recorded.

The composition for influenza prevention and treatment was prepared by mixing 87.5% (w/w) St. John's wort (hypericin content: 0.33%) and 12.5% (w/w) bio-transformed soy (from Ultra Biotech Limited). The St. John's wort was used as the anti-virus agent and the bio-transformed soy as the immune enhancer. This composition was used for all the tests shown in all the following examples except otherwise indicated.

The results are summarized in Table 1 and displayed below. As shown, when the initial H9N1 concentration was 500 pfu/well and received no treatment, the H9N1 concentration increased substantially after three days, denoted as too numerous to count (TNTC), which indicated that the viruses populated. Comparatively, under the same initial conditions but when the composition was administered, the H9N1 concentration significantly decreased after a three-day treatment, which indicated that most of the viruses lost the viability. At a higher concentration of the administered composition, a lower H9N1 concentration was observed after a three-day treatment, hence suggesting that at higher concentrations of the composition, more viruses had lost their viability. Similar trends were also observed when the initial H9N1 concentrations were at 50 and 5 pfu/well. Consequently, these results show that the composition has an anti-viral efficacy towards H9N1, with higher concentrations of the composition exhibiting higher efficacy.

TABLE 1

In-vitro results of anti-virus (H9N1) effect of the composition

| Initial H9N1 conc. | H9N1 conc. (pfu/well) after 3-day treatment with the composition at: | | | |
|---|---|---|---|---|
| (pfu/well) | 200 ppm | 40 ppm | 8 ppm | 0 ppm |
| 500 | 32 | 147 | 176 | TNTC |
| 50 | 1 | 6 | 7 | 21 |
| 5 | 0 | 0 | 0 | 2 |
| 0.5 | 0 | 0 | 0 | 0 |

EXAMPLE 2

Flu Virus (H9N1) Tests in Chicken Embryos

A saline solution was used to dilute the composition for influenza prevention and treatment to 8, 200 and 1000 ppm, respectively. The H9N1 virus (at 10e-4) was mixed with different concentrations of the composition at a ratio of 1:9, and inoculated into the chicken embryos at a rate of 0.2 ml per embryo. For the virus control, the saline solution was used in the place of the composition solution. In addition, only the saline solution without H9N1 virus was incubated into the embryos as the non-challenged control. All the samples were then incubated at 37° C. and observed for embryo viability.

The results were displayed in Table 2. When the chicken embryos were presented the H9N1 virus challenge and received no treatment, about 75 percent of them had lost their viability by day 3 and all of them were not viable by day 4. This represented the virus control. When the chicken embryos were presented the H9N1 virus challenge and received 8 ppm of the composition, only about 34 percent of them had lost their viability by day 3. When the chicken embryos were presented the H9N1 virus challenge and received 200 ppm of the composition, only about 34 percent of them had lost the viability by day 6. When the chicken embryos were presented the H9N1 virus challenge and received 1000 ppm of the composition, all of them were still alive by day 8. When the chicken embryos were not presented the H9N1 virus challenge and no treatment, all of them were also still alive by day 8.

TABLE 2

Protection against H9N1 Virus Challenge in Chicken Embryos

| | Percent embryo survival at | | | | | | | |
|---|---|---|---|---|---|---|---|---|
| Treatments | Day 0 | Day 1 | Day 2 | Day 3 | Day 4 | Day 5 | Day 6 | Day 7 |
| 1000 ppm composition | 100 | 100 | 100 | 100 | 100 | 100 | 100 | 100 |
| 200 ppm composition | 100 | 100 | 100 | 100 | 100 | 100 | 66.7 | 66.7 |
| 8 ppm composition | 100 | 100 | 100 | 66.7 | 66.7 | 66.7 | 66.7 | 66.7 |
| Virus control | 100 | 100 | 25 | 0 | 0 | 0 | 0 | 0 |
| Non-challenged control | 100 | 100 | 100 | 100 | 100 | 100 | 100 | 100 |

As seen, at higher concentrations of the composition treatment, more chicken embryos had lived. Consequently, the results show that the composition can protect the chicken embryos against H9N1 virus, with higher concentration of the composition demonstrating higher efficacy.

EXAMPLE 3

Flu Virus (H9N1) Tests in Mice

Female ICR mice with the weight of 20 to 22 g were used in this study, and H9N1 virus was used as an indicator of the flu virus. The mice were first fed with the composition for influenza prevention and treatment at different dosages for 7 days, and then challenged with H9N1 virus through their eyes and noses. The composition was given to the mice for another 14 days after the virus challenge. The virus control and healthy mice control studies were also conducted at the same time. The detailed information about the eight treatments in this study was as follows:

| Treatment # | Treatment/Composition dosage |
|---|---|
| 1 | 2.25 mg/mouse/day, the composition of the present invention |
| 2 | 1.03 mg/mouse/day, the composition without immune enhancer |
| 3 | 1.22 mg/mouse/day, the composition without anti-virus agent |
| 4 | 0.32 mg/mouse/day, the composition of the present invention |
| 5 | 0.145 mg/mouse/day, the composition without immune enhancer |
| 6 | 0.17 mg/mouse/day, the composition without anti-virus agent |
| 7 | virus control, without feeding the mice with the composition |
| 8 | healthy mice, without H9N1 challenge |

Figure 1:
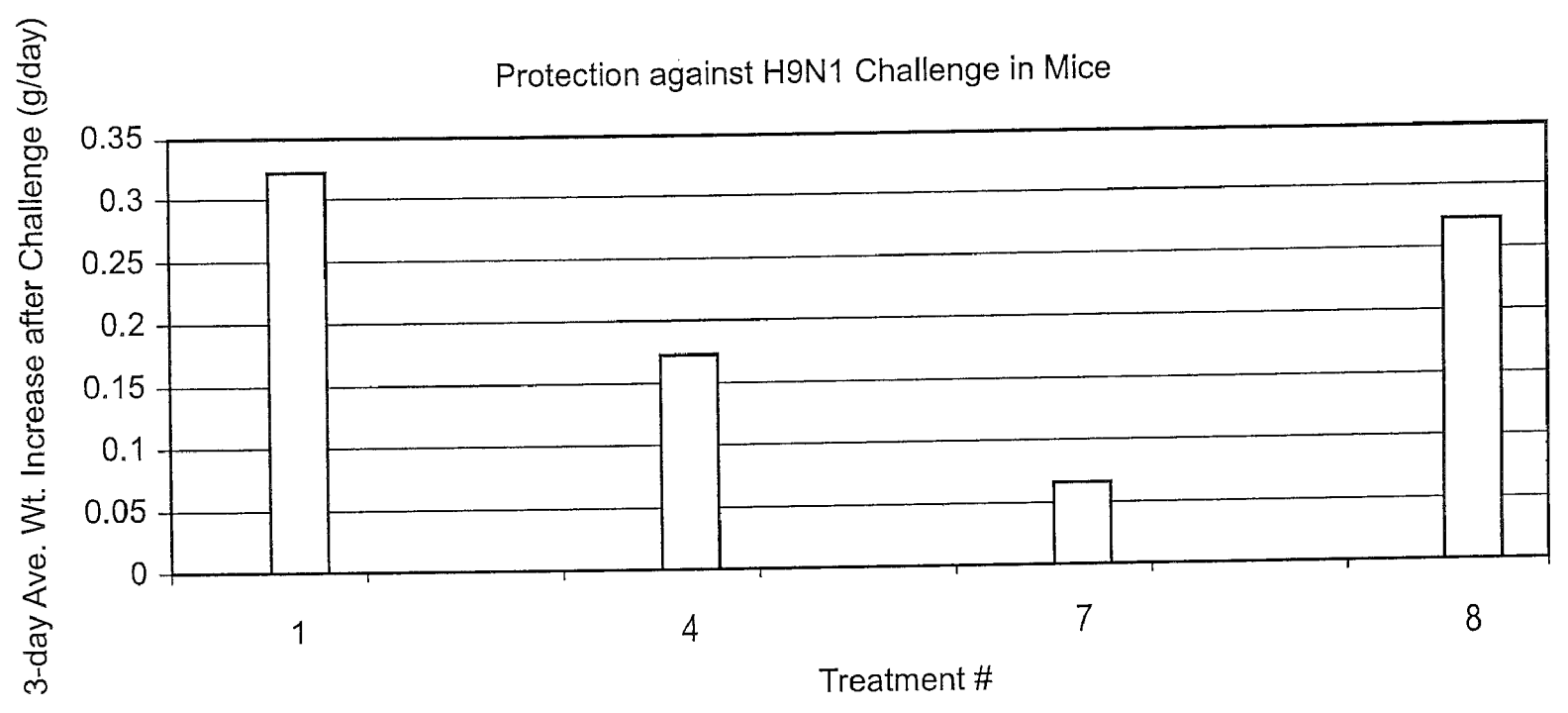

Fifteen mice were used in each treatment. The body weight of each mouse was measured before and after virus challenge. In this experiment, the effectiveness of the composition was determined by the health of the mice, which was measured in terms of the three-day average weight increase—a larger weight increase signifies better health. The efficacy of the components of the composition was also determined, by treating the mice with the composition having and lacking different components. The test results are summarized in FIGS. 1 and 2.

Referring to FIG. 1, the efficacy of the composition was determined. When the mice were not presented the H9N1 challenge, the three-day average weight increases was about 0.27 grams per day. This represented the average weight increase for healthy mice. When the mice were presented the H9N1 challenge and received no treatment, the three-day average weight increase was about 0.06 grams per day. This represented the average weight increase for virus infected mice, and as expected was substantially lowered than that for healthy mice. When the mice were presented the H9N1 challenge and received the composition at 0.32 miligrams per mouse per day, the three-day average weight increase was about 0.17 grams per day. When the mice were presented the H9N1 challenge and received the composition at 2.25 miligrams per mouse per day, the three-day average weight increase was about 0.33 grams per day.

As shown, of the infected mice, those that received the composition demonstrated a higher average weight increase than those that did not. The average weight increased more significantly at a higher concentration of the composition administered. Furthermore, the composition administered at 2.25 miligrams per mouse per day was found to match the average weight increase of the healthy mice. Consequently, the results show that the composition can protect the mice against H9N1 virus challenge.

Referring to FIG. 2, the efficacy of the composition having both the immune enhancer and the anti-viral agent and the composition without the immune enhancer was compared. The conditions for and results of the healthy and infected mice were identical to those as shown in FIG. 1.

When the mice were presented the H9N1 challenge and received the composition at 0.32 miligrams per mouse per day without the immune enhancer, the three-day average weight increase was about 0.05 grams per day. This was substantially lower than that obtained by the composition with the immune enhancer at similar conditions. When the mice were presented the H9N1 challenge and received the composition at 2.25 miligrams per mouse per day without the immune enhancer, the three-day average weight increase was about 0.17 grams per day. This was also substantially lower than that obtained by the composition with the immune enhancer at similar conditions.

Consequently, the composition with both the immune enhancer and anti-viral agent shows superior protection against H9N1 infection than the composition without the immune enhancer. Moreover, at 0.32 miligrams per mouse per day without the immune enhancer, the average weight increase was found to be similar to the infected mice, thus, it can be inferred that the composition without the immune enhancer at low concentration was ineffective to protect against H9N1 infection. At 2.25 miligrams per mouse per day without the immune enhancer, the average weight increase was found to be significantly higher than the infected mice, but was still much lower than the healthy mice, thus suggesting the composition without the immune enhancer cannot sufficiently protect against H9N1 infection.

The efficacy of the composition having both the immune enhancer and the anti-viral agent and the composition without the anti-viral agent was also compared. The conditions for and results of the healthy and infected mice were identical to those as shown in FIG. 1.

When the mice were presented the H9N1 challenge and received the composition at 0.32 miligrams per mouse per day without the anti-viral agent, the three-day average weight increase was about 0.07 grams per day. This was substantially lower than that obtained by the composition with the anti-viral agent at similar conditions. When the mice were presented the H9N1 challenge and received the composition at 2.25 miligrams per mouse per day without the anti-viral agent, the three-day average weight increase was about 0.21 grams per day. This was also substantially lower than that obtained by the composition with the anti-viral agent at similar conditions.

Consequently, the composition with both the immune enhancer and anti-viral agent shows superior protection against H9N1 infection than the composition without the anti-viral agent. Moreover, at 0.32 miligrams per mouse per day without the anti-viral agent, the average weight increase was found to be similar to the infected mice, thus, it can be inferred that the composition without the anti-viral agent at low concentration was ineffective to protect against H9N1 infection. At 2.25 miligrams per mouse per day without the anti-viral agent, the average weight increase was found to be significantly higher than the infected mice, but was still much lower than the healthy mice, thus suggesting the composition without the anti-viral agent cannot sufficiently protect against H9N1 infection.

EXAMPLE 4

In-Vitro Tests—Cytokine (TNF-α) Secretion

The efficacy of the composition and the composition without the immune enhancer was further compared and observed in another in-vitro test as measured by the amount of the TNF-α secretion induced. The filtrates were obtained by filtering the solution of the compositions through 0.22 μm filters.

THP-1 cells (peripheral blood; monocyte; acute monocytic leukemia) were used in the experiment. The cells were cultivated in RPMI 1640 medium for 4-5 days to reach the required cell number. $5 \times 10^5$ of the cells were then seeded into each of the 24-well plate containing RPMI 1640 medium. Triplicate tests were performed for each concentration of the composition. The 24-well plate containing THP-1 cells and the composition filtrates were incubated at 37° C. in a $CO_2$ incubator for 4 hours. 500 µl of the supernatant in each well was then collected by centrifugation at 2500 rpm for 5 minutes and stored at −80° C. freezer until the assay for TNF-α cytokine was performed. The concentration of TNF-α in the THP-1 cell supernatants was measured by an enzyme linked immunosorbent assay (ELISA) according to the technical data sheet of the BD Biosciences TNF-α testing kit.

Figure 3:
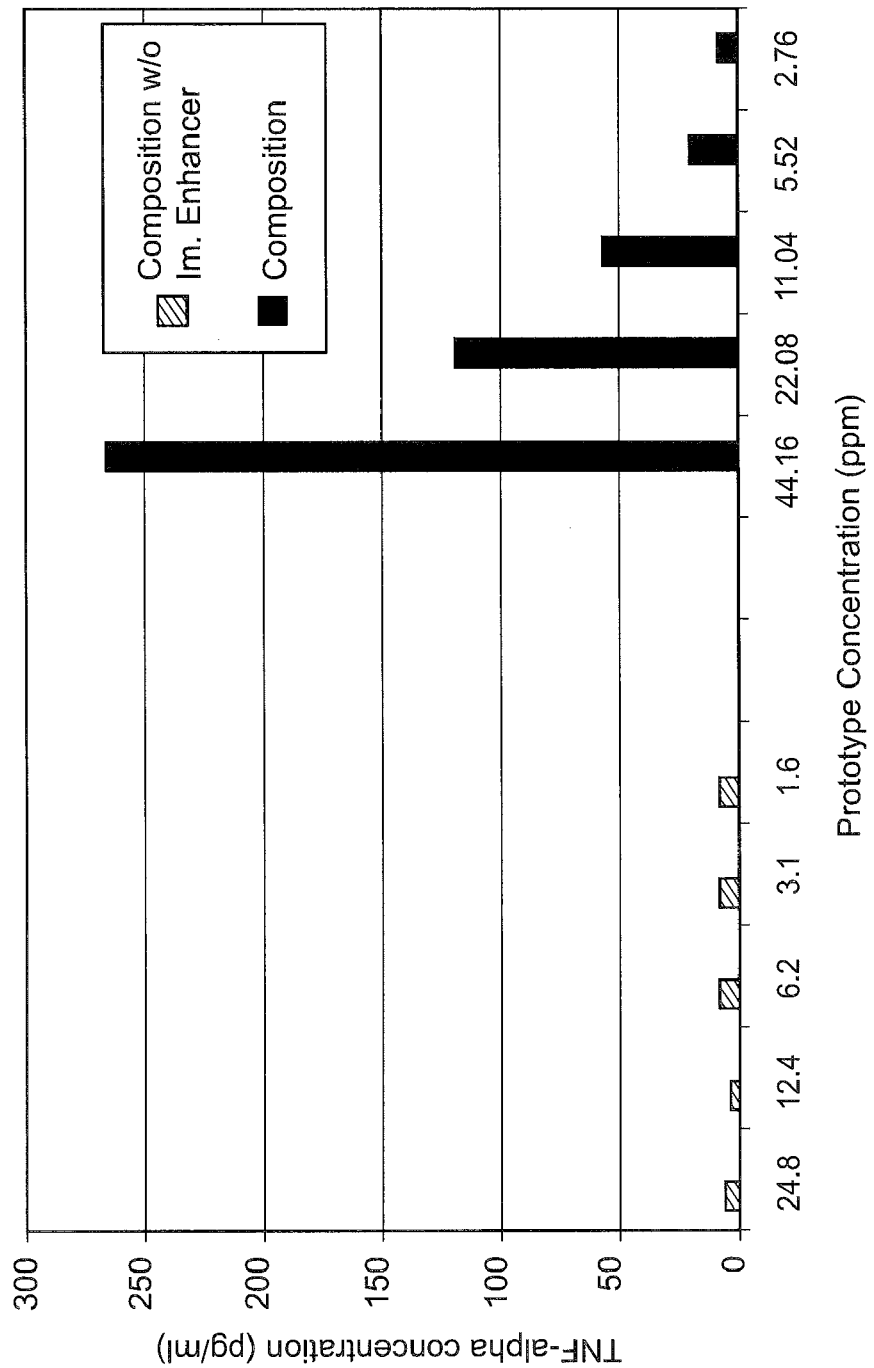
FIG. 3 depicts the efficacy of the composition to induce TNF-$\alpha$ secretion.

Referring to FIG. 3, across all prototype concentrations, those cells treated by the composition with the immune enhancer produced higher TNF-α concentration than those without the immune enhancer. At higher composition concentrations, the differences were even more pronounced, with the composition substantially out-performing the composition without the immune enhancer.

Consequently, the results show that the composition with the immune enhancer induces more TNF-α secretion than the composition without the immune enhancer, and with higher composition concentration producing a more significant effect.

EXAMPLE 5

Flu Virus (H5N1) Tests in Mice

Female balb/c mice (with weight of 20-22 g) were used in this study. The composition of the present invention was fed at different dosages into the mice for 14 days. On day 8, the mice were infected with avian flu H5N1-A virus through their noses. As a positive control, an anti-flu drug, Adamantane, was given to the mice in the place of the composition. In addition, a saline solution was used in the place of the composition as a negative (virus) control. The mice were observed for 21 days and their activity and death were recorded.

The results were displayed in Table 3. When the mice were presented the H5N1 virus challenge and received no treatment, the mice were dying rapidly; about 80 percent of them had died by day 10 and all of them had died by day 11. This represented the virus control. When the mice were presented the H9N1 virus challenge and received Adamantane at 0.4 miligrams per mouse, the mice were also dying rapidly, although at a slower pace: about 70 percent of them had died by day 11 and 80 percent of them had died by day 13.

When the mice were presented the H5N1 virus challenge and received the composition at 0.2 miligrams and at 1.4 miligrams per mouse, respectively, the mice stopped dying after day 10, and about 60 of them were still alive by day 14. This shows a large improvement over the adamantane treatment. Consequently, the results show that the composition can be effective to counter H5N1 virus.

EXAMPLE 6

Process of Making Bio-Transformed Soy

Approximately ten grams of food (soil which could also be used) was added to 30 ml of distilled water, and the resultant mixture was shaken vigorously. The suspension was plated on nutrient agar plate and incubated at 30° C. for 24-48 hrs. Bacterial colonies were isolated and characterized by their colony types, Gram staining, spore formation, and growth conditions. The colonies were initially screened for their abilities of inducing secretion of TNF-alpha according to the following described procedure but in a smaller testing scale. The colonies which resulted in bio-transformed soy with higher effects on TN-alpha secreting were selected as bacterial isolates for large scale production. The selected bacterial isolates were used to prepare culture nutrient agar slants and stored at 4° C. and used for the following fermentation.

Fifty g soybean powder, 0.4 g yeast extract paste, 1 g calcium carbonate, 0.2 g sodium chloride, 0.2 g magnesium sulphate, 0.5 g di-basic potassium phosphate, 0.05 g zinc sulphate, and 0.01 g sodium molybdate were dissolved in 1 liter of water. This liquid medium was contained in a shake flask and autoclaved at 121° C. for 30 minutes. After cooling down, a selected bacterial strain (as mentioned above) was used to inoculate the medium for fermentation. The fermentation was performed on a shaker at 30° C. and with agitation speed of 100 to 300 rpm. The fermentation was continued until the pH of the culture medium reached greater than 8.5. The fermentation culture was then concentrated two times using a rotary evaporator at not higher than 80° C. A filler, such as beta-cyclodextran, was added into the culture concentrate, followed by spray drying (inlet air temperature at 210±20° C.) to obtain a powder product.

Figure 4:
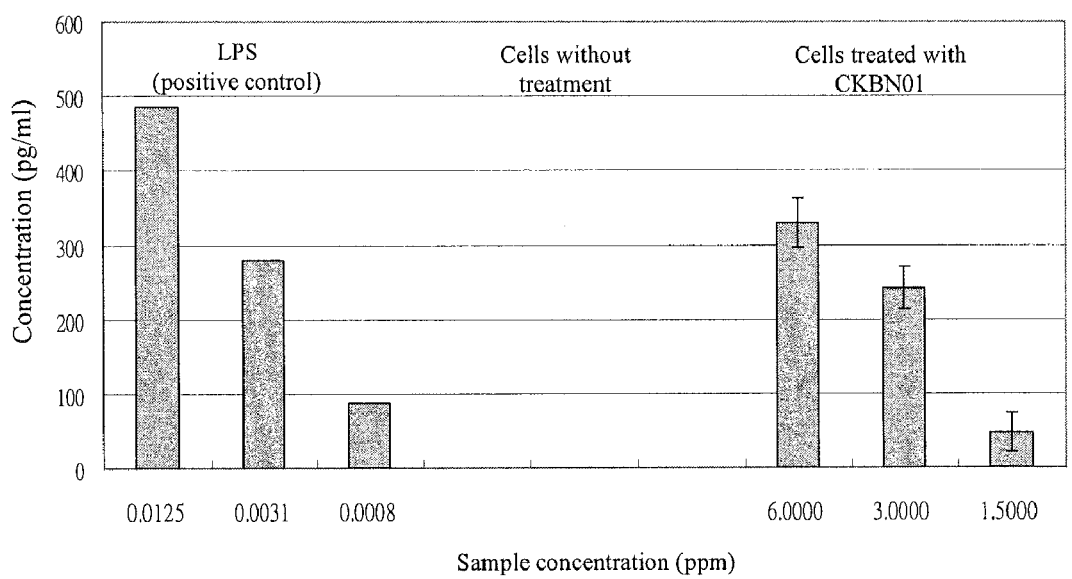
FIG. 4 is an example of the TNF-alpha assay results on the bio-transformed soy (code named as CKBN01).

The powder product prepared according to the above procedure was then tested for secretion of a cytokine, TNF-alpha, which was used as indication of the immune-enhancing activity of the biotransformed soy. The TNF-alpha assay was conducted using a procedure listed below (however, a person of ordinary skill in the art may choose to use other available methods for conducting the assay). When the secretion of TNF-alpha concentration of the biotransformed soy sample at 50 ppm was greater than that of LPS (lipopolysaccharide) standard at 10 ng/ml, the biotransformed soy was considered to be qualified for being used as an immune-enhancing agent to prepare the composition of this invention. An example of the TNF-alpha assay results from the biotransformed soy is shown FIG. 4.

| Treatments | Percent mouse survival at | | | | | | | | |
| --- | --- | --- | --- | --- | --- | --- | --- | --- | --- |
|  | Day 0 | Day 7 | Day 8 | Day 9 | Day 10 | Day 11 | Day 12 | Day 13 | Day 14 |
| 1.4 mg composition per day per mouse | 100 | 90 | 90 | 80 | 60 | 60 | 60 | 60 | 60 |
| 0.2 ppm composition per day per mouse | 100 | 90 | 90 | 60 | 60 | 60 | 60 | 60 | 60 |
| 0.4 mg Adamantane per day per mouse | 100 | 90 | 80 | 60 | 40 | 30 | 30 | 20 | 20 |
| Virus control | 100 | 90 | 80 | 50 | 20 | 0 | 0 | 0 | 0 |

EXAMPLE 7

Determination of TNF-Alpha Secretion using ELISA Assay

The objective of this procedure is for determination of TNF-alpha secretion in biotransformed soy related products. The procedure involves sample treatment with THP-1 cells and the determination of TNF-alpha secretion using ELISA assay.

Reagents 1.1 Complete growth RPMI medium 1640 with glucose (refer to references 7.1); 1.2 LPS (Sigma, cat. No. L2654 or equivalent); 1.3 THP-1 cells; 1.4 BD OptEIA Human TNF ELISA Set (BD Biosciences, cat. No. 555212 or equivalent); 1.5 OptEIA Reagent Set B (BD Biosciences, cat No. 550534 or equivalent); and 1.6 De-ionized water (18.2M$\Omega$).

Apparatus 2.1 Shaking water bath; 2.2 $CO_2$ incubator, Shel Lab 2424-2 or equivalent; 2.3 Inverted microscope, Leica DMIL or equivalent; 2.4 Ultrasonic bath; 2.5 Analytical balance; 2.6 Laminar Flow Biological safety cabinet, Nuair NU-425-400E or equivalent; 2.7 Vortex mixer; 2.8 Microplate, 96-well with lid; 2.9 0.22 um sterilized syringe filter; 2.10 ELISA plate reader; 2.11 Refrigerator/Freezer (−20° C.); 2.12 -80° C. freezer; 2.13 F96 Maxisorp Immune plate; 2.14 Sealing film; 2.15 Centrifuge; 2.16 Automated washer with 2 L plastic bottle; and 2.17 Timer Sample Preparation 3.1 Dissolve 0.1 g of the powder sample with 10 ml of de-ionized water and sonicate the solution in the ultrasonic bath for 40 minutes. The sample size should be adjusted if necessary.

3.2 Centrifuge the sample solution at 3000 rpm for 5 minute. Further filter the supernatant with 0.22 um sterilized syringe filter.

3.3 Serial dilute the testing samples with the complete growth RPMI medium 1640 with glucose appropriately.

3.4 For each sample, add 100 ul of diluted samples into the 96-well plate. Add samples into 3 wells for each dilution as triplicates LPS Standard Preparation 4.1 Add 1 ul of 100 ug/ml LPS into 999 ul of the growth medium to make 100 ng/ml standard solution.

4.2 Serial dilute the resulting solution appropriately 4.3 Add 100 ul each of diluted LPS solutions into the 96-well plate. Add the solution into 3 wells for each dilution as triplicates.

4.4 For negative control, add 100 ul of the growth medium into 3 wells of the plate.

Cultivation of Treated THP-1 Cells 5.1 Adjust the concentration of THP-1 cells to $1 \times 10^6$ cells per ml with the fresh growth medium.

5.2 Add 100 ul of the THP-1 cells into each well of the plate loaded with samples and LPS solutions.

5.3 Cultivate the treated cells into the 37° C., 5% $CO_2$ incubator for 4 hours.

5.4 After incubation, centrifuge the plate at 2500 rpm for 5 minutes and then transfer the suspension into the new 96-well plate.

5.5 Store the plate at −20° C. freezer before proceed the TNF-alpha measurement.

ELISA Plate Preparation 6.1 Bring all reagents and samples to room temperature before use.

6.2 Pipette 40 ul of capture antibody into 10 ml of coating buffer to prepare the working capture antibody solution for a full 96-well Immune plate.

6.3 Coat each well with 100 ul of working capture antibody solution and incubate the plate overnight at 4° C.

6.4 Prepare 1× wash buffer solution by diluting 100 ml of 20× wash buffer to 2 L with de-ionized water into 2 L reagent bottle. Mix well and transfer the solution to the automated washer bottle.

6.5 Aspire the solution of the coated plate and wash all the wells three times with 1× wash buffer solution. Invert the plate and blot on absorbent paper to remove any residual buffer after the last wash.

6.6 Block the plate with 200 ul per well of assay diluent and incubate the plate at room temperature for 2 hours.

6.7 Repeat the plate washing for three times after incubation.

Assay Procedure 7.1 Reconstitute the lyophilized TNF-alpha standard with 1 ml of de-ionized water to yield a stock standard after warmed to room temperature. Allow the standard to equilibrate for at least 15 minutes before making the dilution. The stock standard should be stored in −80° C. freezer.

7.2 Prepare a 500 pg/ml of TNF-alpha standard dilution from the stock standard.

7.3 Perform a series of two fold dilutions by mixing 500 ul of each standard with 500 ul of assay diluent.

7.4 Using the assay diluent as the zero standard (0 pg/ml).

7.5 Pipette 100 ul of standards and samples into the wells of coated plate. Shake the plate for several seconds. Cover the wells with sealing film and incubate the plate at room temperature for 2 hours.

7.6 Repeat plate washing for 5 times after incubation.

7.7 Prepare the working detector solution by mixing 40 ul of detection antibody and 40 ul of enzyme reagent to 10 ml of assay diluent for a full 96-well plate 15 minutes prior use.

7.8 Add 100 ul of prepared working detector solution into each well. Cover the wells with sealing film and incubate the plate at room temperature for 1 hour.

7.9 Repeat plate washing for 7 times after incubation.

7.10 Prepare substrate reagent freshly by mixing 5 ml of substrate reagent A and 5 ml of substrate reagent B for a full 96-well plate. Place the solution in the dark before use.

7.11 Add 100 ul of substrate reagent to each well and incubate for 30 minutes at room temperature in the dark without sealing film.

7.12 Add 50 ul of stop solution to each well and mix well after incubation.

7.13 Read the absorbance at 450 nm and 570 nm (background correction) within 30 minutes after adding the stop solution.

Calculation/Result Interpretation 8.1 Plot the linear calibration graph for the absorbance against TNF-alpha standard concentration.

8.2 Determine the TNF-alpha concentration of the samples and LPS solutions from the graph.

8.3 Plot the calibration graph for the TNF-alpha concentration induced against Natural logarithm (Ln) of LPS concentration.

8.4 Determine the LPS concentration (ng/ml) which induces the TNF-alpha concentration is equivalent to those of the sample at 50 ppm.

Quality Control Parameters

The correlation coefficient r2 of the calibration curve is not less than 0.9.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method for treating influenza in a patient in need thereof consisting essentially of
    administering to the patient a therapeutically effective amount of a soybean extract and a St. John's wort extract.

2. The method according to claim 1, wherein the St. John's wort extract is hypericin.

3. The method according to claim 1, wherein the St. John's wort extract is in a dosage of 20 mg to 5,000 mg.

4. The method according to claim 1, wherein the St. John's wort extract is in a dosage of 100 mg to 2,000 mg.

5. The method according to claim 1, wherein the St. John's wort extract is from 5 to 95 weight percent.

6. The method according to claim 1, wherein the therapeutically effective amount of the soybean extract and the St. John's wort extract is administered to the patient in a form selected from the group consisting of a tablet, a capsule, and a liquid.

7. The method according to claim 2, wherein the St. John's wort extract is 0.3% w/w hypericin.

* * * * *